(12) United States Patent
Ika et al.

(10) Patent No.: US 8,290,786 B2
(45) Date of Patent: Oct. 16, 2012

(54) PROSPECTIVE HEALTH CARE QUALITY IMPROVEMENT

(76) Inventors: Ravi Ika, Southboro, MA (US);
Solomon Zak, St. Louis Park, MN (US);
Rudra Duddala, Westboro, MA (US);
James Poladas, Worcester, MA (US)

( * ) Notice: Subject to any disclaimer, the term of this patent is extended or adjusted under 35 U.S.C. 154(b) by 863 days.

(21) Appl. No.: 11/895,319

(22) Filed: Aug. 25, 2007

(65) Prior Publication Data
US 2009/0055218 A1  Feb. 26, 2009

(51) Int. Cl.
*G06Q 10/00* (2012.01)
(52) U.S. Cl. ................................. 705/2; 705/3
(58) Field of Classification Search ....................... 705/2
See application file for complete search history.

(56) References Cited

U.S. PATENT DOCUMENTS

| | | | | |
|---|---|---|---|---|
| 5,845,254 A | * | 12/1998 | Lockwood et al. | 705/2 |
| 5,924,073 A | * | 7/1999 | Tyuluman et al. | 705/2 |
| 6,151,581 A | * | 11/2000 | Kraftson et al. | 705/3 |
| 2002/0111826 A1 | * | 8/2002 | Potter et al. | 705/2 |
| 2007/0192132 A1 | * | 8/2007 | Thesman | 705/2 |

* cited by examiner

*Primary Examiner* — Hiep V Nguyen
(74) *Attorney, Agent, or Firm* — Ash Tankha; Lipton, Weinberger & Husick (57) ABSTRACT

Disclosed herein is a computer implemented method and system for improving the quality of health care in a health plan. The members of the health plan eligible for undergoing predetermined measures of health care are identified. The primary care physicians (PCPs) for the identified members are notified to ensure implementation of the predetermined measures. The health plan staff is notified to ensure coordination between the identified members and PCPs. The status of the identified members is updated based on the implemented predetermined measures. Quality indexes for the PCPs are calculated for the implemented predetermined measures. A performance score of the health plan is calculated to indicate the quality of health care. Identifying and notifying the members, the PCPs and the health plan staff reduces the level of clinical chart review by the health plan staff and improves the quality of health care in a health plan.

26 Claims, 6 Drawing Sheets

| Member Id : | 36103616*01 |
| Member Name : | |
| Measure Name : | 3 CHILDHOOD HEPATITIS B |
| Measure Value : | |
| Measure Date : | (MM/DD/CCYY) |
| Measure Source : | Patient Chart |
| Signature : | 501 |

[Cancel] [Update]

FIGURE 5

HEDIS Analysis

| Description Type | 4DPT+ 3OPV+ 1MMR+ 3HIB+ 3HEP. B+ 1VZV | 4DPT+ 3OPV+ 1MMR+ 3HIB+ 1HEP. B+ 1VZV+ 4PNEUMO | 4 CHILDHOOD DPT | 3 CHILDHOOD OPV | 3 CHILDHOOD INFLUENZA TYPE B | 3 CHILDHOOD HEPATITIS B | 1 CHILDHOOD MMR | 1 CHILDHOOD VZV | 4 CHILDHOOD PNEUMO |
|---|---|---|---|---|---|---|---|---|---|
| PLAN | 782/3843 | 707/3843 | 2147/3843 | 2487/3843 | 2869/3843 | 996/3843 | 3351/3843 | 3324/3843 | 2207/3843 |
| SUMMARY | - 19.57% | - 18.4% | - 55.87% | - 64.72% | - 74.63% | 25.97% | - 87.2% | - 86.49% | - 57.43% |
| NATIONAL BENCHMARK | 20% | 25% | 73% | 73% | 73% | 73% | 73% | 73% | 73% |

Email/Fax Reminder

○ List of PCP(s) < 50% ZCP

○ List of PCP(s) < 50% National Benchmark

[Email] [Fax]

FIGURE 6

| PCPs | Measure 1 (Eligible Population) | Measure 1 (Eligible Population already Measured) | Index of PCP/Plan for Measure 1 | Measure 2 (Eligible Population) | Measure 2 (Eligible Population already Measured) | Index of PCP/Plan for Measure 2 |
|---|---|---|---|---|---|---|
| PCP1 | 60 | 40 | 40/60 = 0.6 | 75 | 50 | 50/75 = 0.66 |
| PCP2 | 40 | 20 | 20/40 = 0.5 | 125 | 50 | 50/125 = 0.4 |
| Plan | 100 | 60 | 60/100 = 0.6 | 200 | 100 | 100/200 = 0.5 |

PROSPECTIVE HEALTH CARE QUALITY IMPROVEMENT

BACKGROUND

This invention, in general, relates to a method and system of processing information of members and service providers in the health care industry to improve the quality of health care in a health plan.

Health care organizations perform performance tests on existing health plans to determine the quality of health care provided to the members of a health plan. Increased attention to medical care has resulted in the development of a set of standardized measures that specify how health plans collect, audit, and report performance information across clinical areas, and dimensions significant to customer satisfaction and patient experience. A measure is a medical observation or test performed on a member by a health care provider.

A set of standardized performance measures called the Health Plan Employer Data and Information Set (HEDIS) has been developed and maintained by the National Committee for Quality Assurance (NCQA) to allow consumers to compare performance of a health plan to other plans, for Medicare plans and Medicaid plans, and compare employer groups within a health plan in commercial health plans. The performance of the health plan may also be compared to national HEDIS benchmarks or regional, benchmarks. HEDIS data are collected through surveys, medical charts, insurance claims for hospitalizations, medical office visits, and pharmacies. HEDIS results are used for tracking the year-to-year performance of the health plans.

Health plans report the percentage of members requiring specified HEDIS measures. Health plans may provide for collection of data for these measures by reviewing insurance claims or clinical charts of members. This chart review requires manual intervention by health plan staff to determine whether the members have implemented the measures. Moreover, primary care physicians (PCPs) of a health plan need to follow up with their members to ensure the implementation of the measures. Therefore, there is a need for a computer implemented method and system to reduce the level of review of clinical charts by the health plan staff, and improve the quality of health care in a health plan. Such a computer implemented method would proactively notify PCPs and identified members to facilitate implementation of the predetermined measure and notify the health plan staff to coordinate such implementation, and also provide the PCPs the interface to update an implemented measure. Collectively these two methods would increase the performance score of the predetermined measures and reduce the level of chart review thereby improving healthcare quality.

SUMMARY OF THE INVENTION

The computer implemented method and system disclosed herein addresses the need to improve the quality of health care and reduce the level of review of clinical charts by the health plan staff.

The computer implemented method and system disclosed herein identifies members of a health plan eligible for undergoing predetermined measures of health care. The predetermined measures of health care are characterized by the health plan employer data and information set (HEDIS). The primary care physicians (PCPs) for the identified members are also identified. The identified members are then notified to undergo the predetermined measures. The PCPs are notified to ensure implementation of the predetermined measures by the identified members. The health plan staff is also notified to ensure coordination between the identified members and the PCPs, and direct coordination with the identified members without the PCPs.

The computer implemented method and system disclosed herein provides an online user interface for the PCPs to update the status of the identified members based on the implemented predetermined measures. A quality index calculator then calculates quality indexes for the PCPs for the implemented predetermined measures. A performance score of the health plan is also calculated for each of the predetermined measures to indicate the quality of health care in the health plan. The automated identification and notification of the members, the PCPs, and the health plan staff about the predetermined measures, facilitate implementation of predetermined measures thereby increasing the performance score and reducing the level of review of clinical charts by the health plan staff.

The computer implemented method and system disclosed herein enables prospective identification and notification of the members, the PCPs, and the health plan staff. The method disclosed herein, thereby, enables prospective implementation of the predetermined measures providing sufficient time for the PCPs to improve their scores before the plan year end thereby improving the quality of health care provided to its members. The health plan staff ensures coordination between the members and the PCPs to improve the performance score of the PCPs, and ensures direct coordination with the identified members without the PCPs, thereby improving the quality of health care in the health plan.

BRIEF DESCRIPTION OF THE DRAWINGS

The foregoing summary, as well as the following detailed description of the embodiments, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE DRAWINGS

Figure 1:
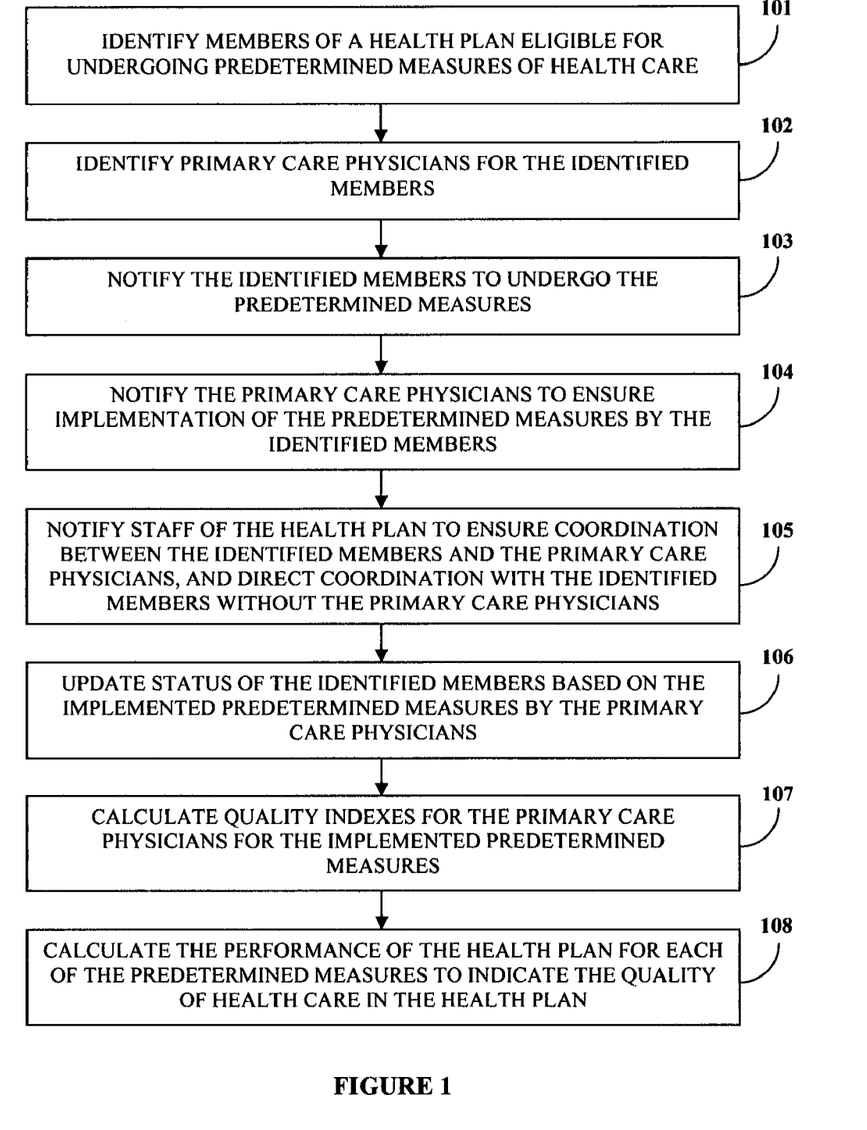
FIG. 1 illustrates a method of improving quality of health care in a health plan.

FIG. 1 illustrates a method of improving quality of health care in a health plan. The computer implemented method disclosed herein identifies 101 members 202 of the health plan eligible for undergoing predetermined measures of health care. The members 202 of the health plan may be one of individual consumers or employees of companies requiring health care, where the companies provide health benefits to the employees. The predetermined measures of health care are defined by the health plan employer data and information set (HEDIS). The HEDIS measures are divided into eight domains namely, effectiveness of care, availability of care, satisfaction with the experience of care, health plan stability, use of services, cost of care, informed health care choices, and health care descriptive information. The HEDIS measures required by the members 202 of the health plan are stored in a health care database 201h.

The HEDIS measures specify how health care organizations collect, audit and report performance information across clinical areas. HEDIS may comprise immunizations, cancer screenings, treatment after heart attacks, diabetes, asthma, flu shots, access to services, dental care, alcohol and drug dependence treatment, timeliness of handling claims and phone calls, prenatal and postpartum care, mental health care, well-care or preventive visits, inpatient utilization, drug utilization, and distribution of members 202 by age, gender, product lines, etc. The members 202 of the health plan eligible for undergoing the predetermined measures of health care may be identified based on their age, gender and pre-existing disease conditions. The eligibility of the members 202 of the health plan is determined using the medical history data of the members 202. The information of the members 202 and the medical history data is stored in a health care database 201h.

The method disclosed herein also identifies 102 the primary care physicians (PCPs) 203 of the identified members 202 of the health plan. The PCPs 203 are usually the first medical practitioners contacted by a member of a health plan due to the ease of communication, accessible location, familiarity, cost issues, and managed care requirements. Many health maintenance organizations position PCPs 203 to provide the members 202 with access to more costly procedures or specialists. The PCPs 203 typically act on behalf of the members 202 to coordinate with referral specialists, coordinate the health care provided by varied organizations such as hospitals or rehabilitation clinics, act as a comprehensive repository for the members' 202 records, and provide long-term management of chronic conditions. Many PCPs 203 follow up on their members 202 in a variety of health care settings such as offices, hospitals, critical care units, long-term facilities, and at home.

The identified members 202 are notified 103 to undergo the predetermined measures. The PCPs 203 of the identified members 202 are notified 104 to ensure implementation of the predetermined measures for the identified members 202. The staff of the health plan 204 is also notified 105 to ensure coordination between the identified members 202 and the PCPs 203, and direct coordination with the identified members 202 without the PCPs 203. The step of notifying the members 202, the PCPs 203, and the health plan staff 204 may be performed by an electronic means including electronic mail (email), fax, and automated voice messages. The step of notifying the members 202, the PCPs 203, and the health plan staff 204 ensure coordination and implementation of the predetermined measures. This step enables the members 202 to undergo preventive measures, for example tests, in order to manage their disease conditions effectively. The disclosed method also provides email addresses and telephone numbers of the members 202 to the PCPs 203 to enable the PCPs 203 to notify members 202 to schedule for the predetermined measures. The email addresses and telephone numbers of the members 202 are stored in the health care database 201h. The automated steps of identifying and notifying the members 202, the PCPs 203, and the health plan staff 204 about the predetermined measures proactively increases the performance scores of the predetermined measures and reduces the level of review of clinical charts by the health plan staff 204.

The status of the identified members 202 are updated 106 based on the implemented predetermined measures by the PCPs 203 using an online user interface. If certain predetermined measures have already been implemented by the identified members 202, the PCP may update the status using the online user interface. Quality indexes for the PCPs 203 for the implemented predetermined measures are calculated 107 to determine the performance of the PCPs 203. The step of calculating the quality indexes for the PCPs 203 comprises calculating an individual quality index for each of the predetermined measures, a relative quality index for each of the predetermined measures compared to the plan's average score for the predetermined measures, and a total quality index for each of the PCPs 203. The total quality index for each of the PCPs 203 may then be used for designing pay for performance (P4P) programs based on the quality of health care. P4P programs in health insurance organizations reward PCPs 203 for meeting certain performance measures for quality and efficiency and for efficient delivery of healthcare services. Effective incentive programs may also be designed to reward the PCPs 203 for good performance. These programs enable the PCPs 203 to consciously aspire to meet the required measures of the health plan and thus also improve the overall quality of the health plan. A performance score of the health plan for each of the predetermined measures is then calculated 108 for indicating the quality of health care in the health plan.

The computer implemented method disclosed herein enables prospective identification and notification of the members 202 and PCPs 203, and the health plan staff 204, and updation of the status of the identified members 202 based on the implemented predetermined measures. The process of implementing the measures as defined by HEDIS ahead of a scheduled time enables the health plan to meet the quality benchmarks required by the National Committee for Quality Assurance (NCQA) for accreditation at the end of the HEDIS plan year. Exemplarily, every year, the NCQA publishes the required measures along with the technical specifications for each measure in the month of July for the current plan year. The computer implemented method disclosed herein implements the required measures of the current plan year in the month of August/September of the current year, thereby providing enough time to complete the measures before the plan year ends in December.

Figure 2:
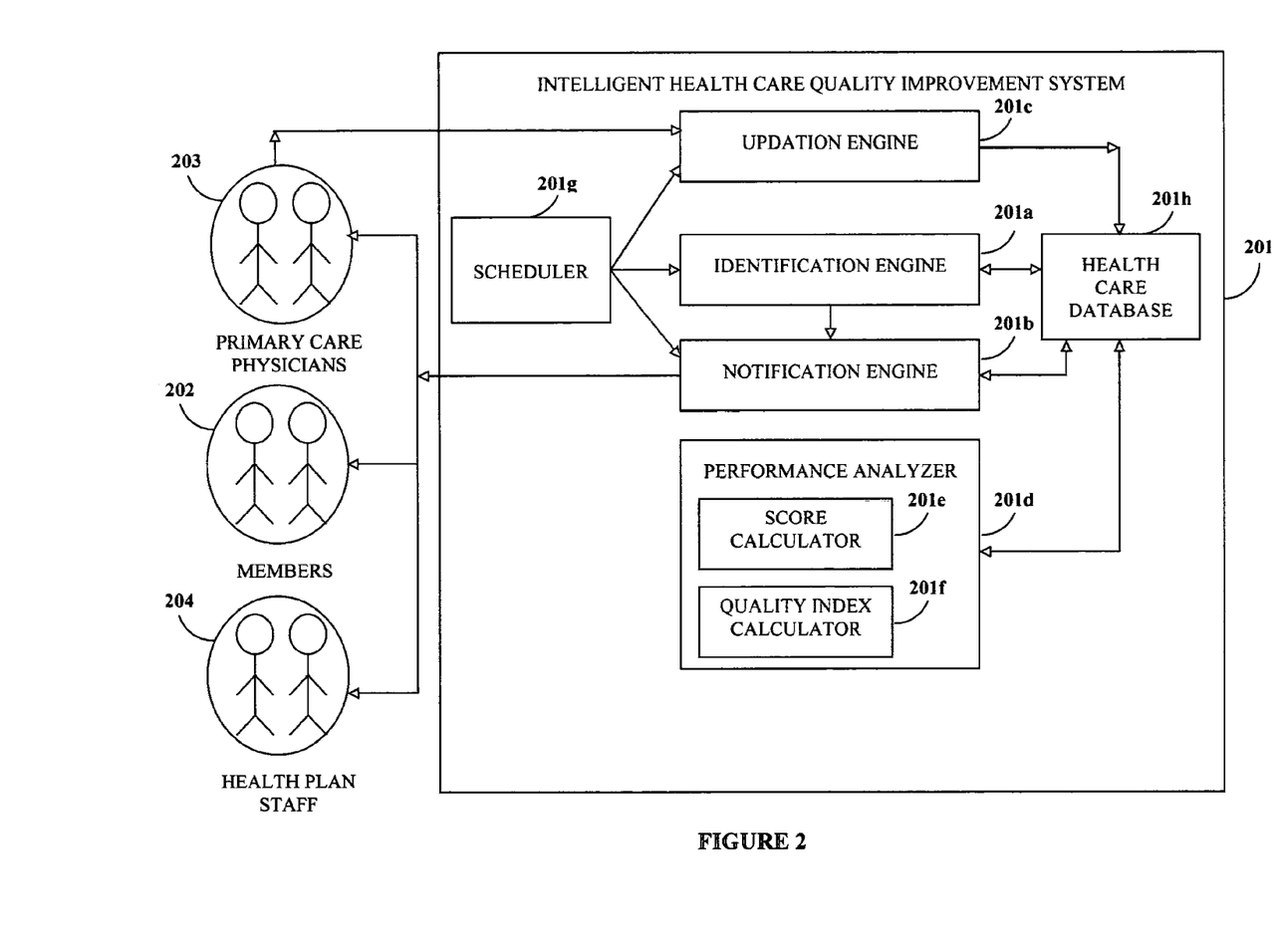
FIG. 2 illustrates a system for improving quality of health care in a health plan.

FIG. 2 illustrates a system for improving quality of health care in a health plan. The computer implemented system disclosed herein comprises an intelligent health care quality improvement system 201 comprising an identification engine 201a, a notification engine 201b, an updation engine 201c, a performance analyzer 201d, a health care database 201h, and a scheduler 201g. The identification engine 201a of the intelligent health care quality improvement system 201 identifies the members 202 of the health plan eligible for undergoing predetermined measures of the health care. The predetermined measures required by the members 202 of the health plan are stored in the health care database 201h. The health care database 201h also stores the information of the members 202, information of the primary care physicians (PCPs) 203, and the performance score of the health plan. The member information comprises names of the members 202, medical history data of the members 202, and status of the members 202 based on the predetermined measures. The PCPs 203 information comprises names of the PCPs 203, the names of the members 202 of the PCPs 203, and the quality indexes of the PCPs 203.

Figure 3A:
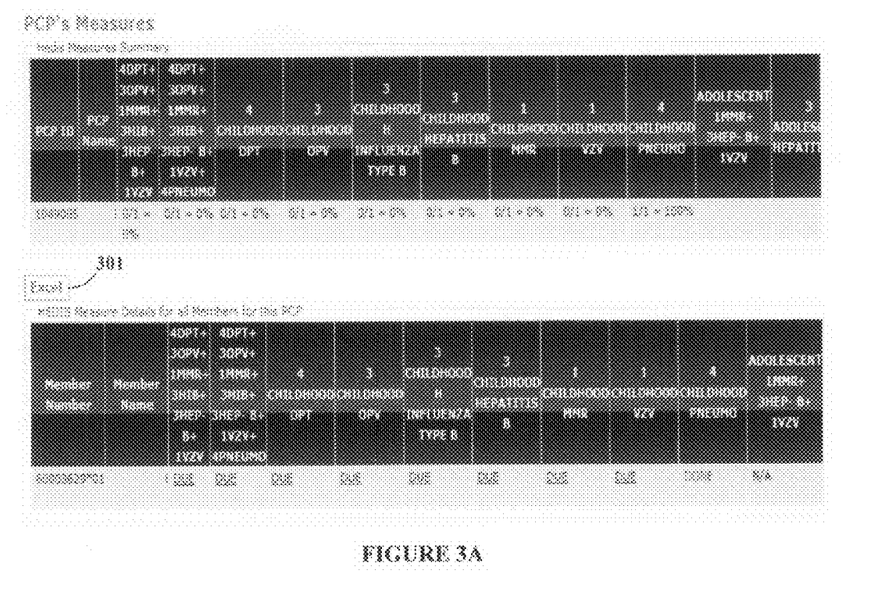
FIG. 3A exemplarily illustrates a screen display of the predetermined measure details for the identified members and the corresponding primary care physicians.
Figure 3B:
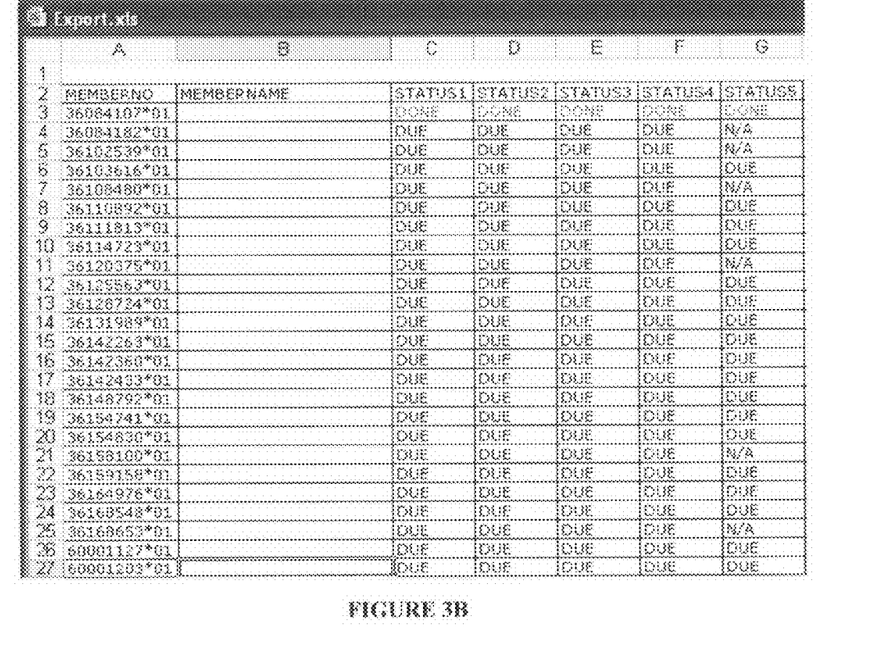
FIG. 3B exemplarily illustrates a list of members eligible for undergoing predetermined measures of health care in a spreadsheet format used for updation by the primary care physicians.

The identification engine 201a also identifies the PCPs 203 for the identified members 202. The scheduler 201g schedules the identification of the members 202 and the PCPs 203 by the identification engine 201a. FIG. 3A exemplarily illustrates a screen display of the predetermined measure details for the identified members 202 and the corresponding primary care physicians 203. By clicking the button 301 illustrated in FIG. 3A, the PCPs 203 are provided with the list of members 202 eligible for undergoing predetermined measures of health care in a spreadsheet format. FIG. 3B exemplarily illustrates a list of members 202 eligible for undergoing predetermined measures of health care in a spreadsheet format for the primary care physicians 203.

Figure 4:
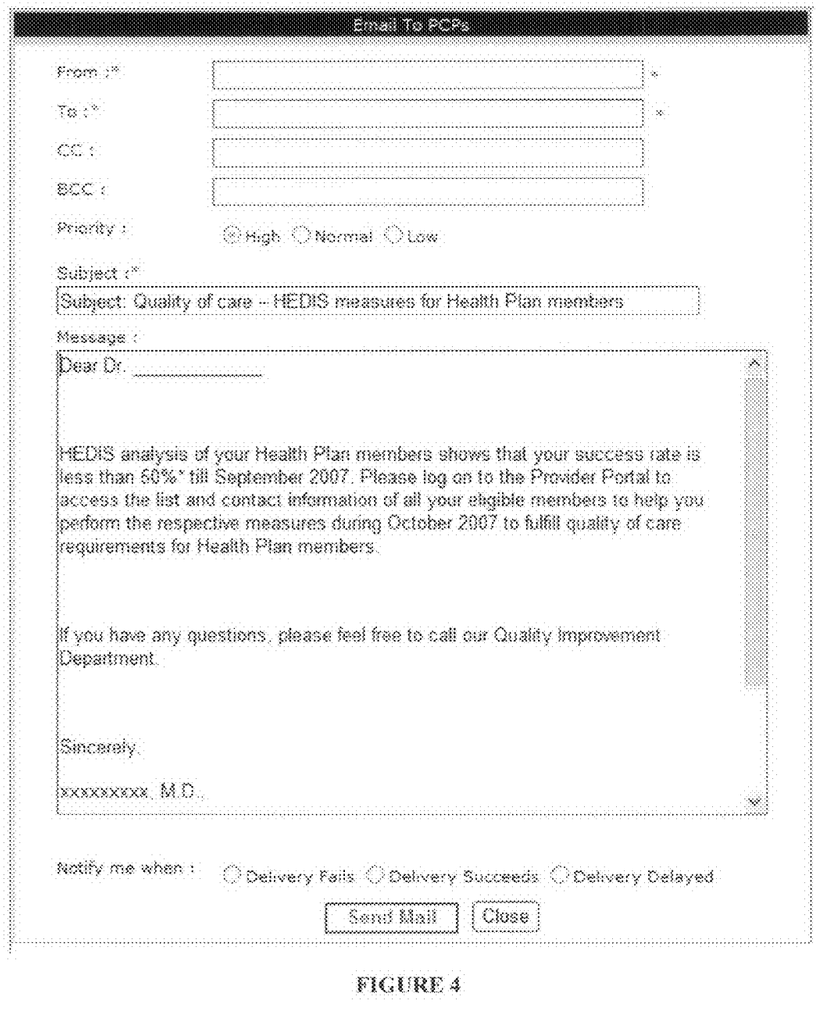
FIG. 4 exemplarily illustrates an electronic mail notification sent to the primary care physicians to ensure the implementation of the predetermined measures.

The notification engine 201b of the intelligent health care quality improvement system 201 notifies the identified members 202 to undergo the predetermined measures. The notification engine 201b also notifies the PCPs 203 to ensure implementation of the predetermined measures by the identified members 202. The health plan staff 204 is also notified to ensure coordination between the identified members 202 and the PCPs 203, and direct coordination with the identified members 202 without the PCPs 203, using the notification engine 201b. The scheduler 201g schedules the notification of the identified members 202, the PCPs 203, and the health plan staff 204 by the notification engine 201b. The PCPs 203 who have not met the required percentage specified by the health plan are notified and reminded to follow-up on the identified members 202. The PCPs 203 may also notify the identified members 202 to schedule for the predetermined measures. The notification engine 201b may notify the members 202, the PCPs 203, and the health plan staff 204 through an electronic means including electronic mail (email), fax, and automated voice messages. FIG. 4 exemplarily illustrates an electronic mail notification sent to the PCPs 203 to ensure the implementation of the predetermined measures. The email addresses and telephone numbers of the members 202 required for the notification are stored in the health care database 201h.

Figure 5:
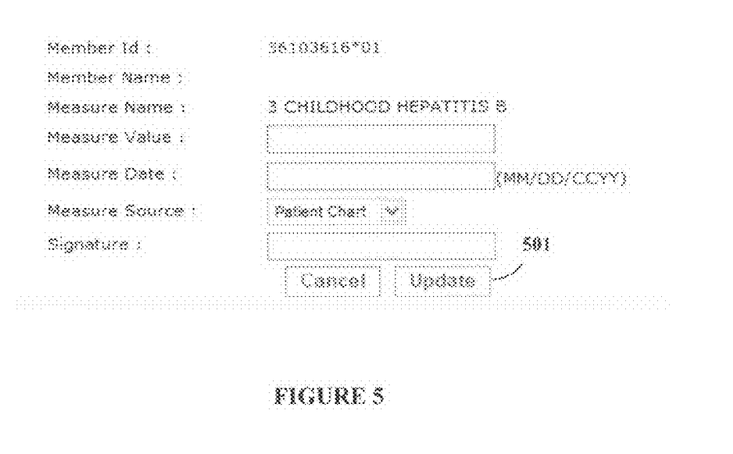
FIG. 5 exemplarily illustrates an online user interface for updating the status of the identified members based on the implemented predetermined measures by the primary care physicians.

The updation engine 201c of the intelligent health care quality improvement system 201 provides an online user interface for the PCPs 203 to update the status of the identified members 202 based on the implemented predetermined measures. The scheduler 201g schedules the updation of the status of the identified members 202 by the updation engine 201c. FIG. 5 exemplarily illustrates an online user interface for updating the status of the identified members 202 based on the implemented predetermined measures by the primary care physicians 203. By clicking the update button 501 provided by the online user interface, the implemented predetermined measures are updated and stored in the health care database 201h.

Figure 6:
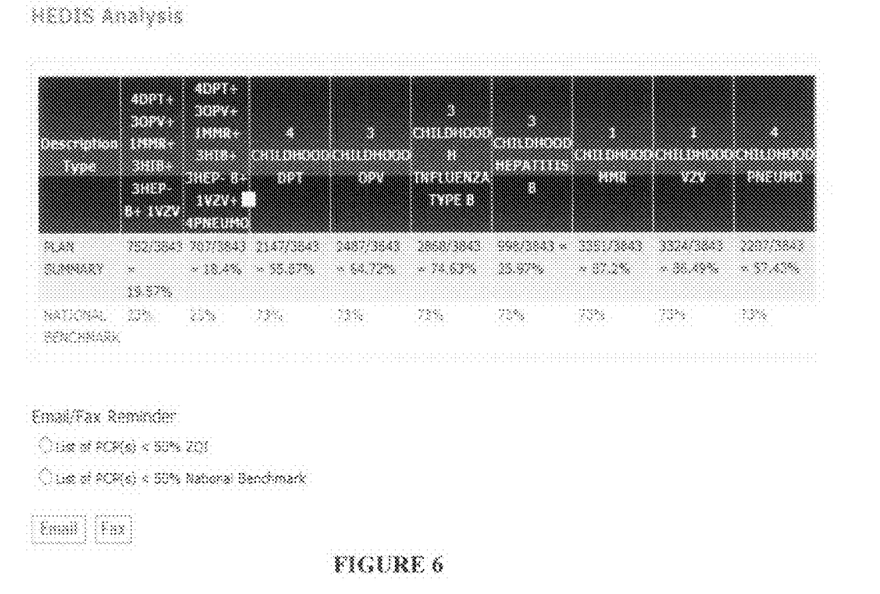
FIG. 6 exemplarily illustrates a screen display of the performance score of the health plan for each of the predetermined measures.

The performance analyzer 201d of the intelligent health care quality improvement system 201 comprises a score calculator 201e and a quality index calculator 201f. The score calculator 201e calculates a performance score of the health plan for each of the predetermined measures. The performance score for a predetermined measure of the health plan is the ratio of the number of the members 202 of the health plan already measured for the predetermined measure to the total number of the identified members 202 for that predetermined measure in the health plan. The performance score is used for comparing performance of the health plan with predetermined performance benchmarks. The predetermined performance benchmarks are one of national benchmarks and regional benchmarks. FIG. 6 exemplarily illustrates a screen display of the performance score of the health plan for each of the predetermined measures.

Figure 7A:
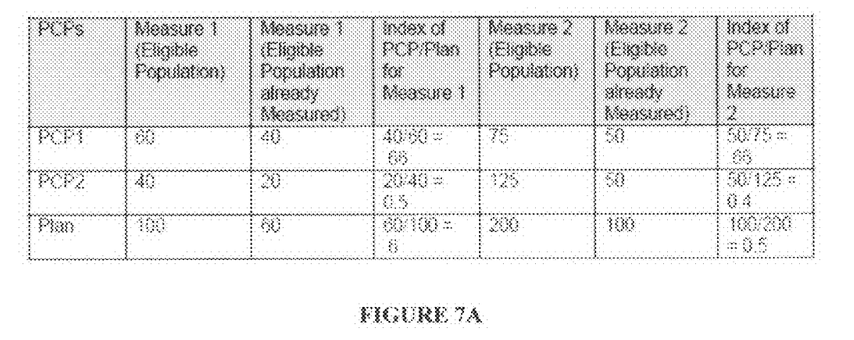
FIG. 7A exemplarily illustrates the calculation of the quality indexes for the primary care physicians for the implemented predetermined measures.
Figure 7B:
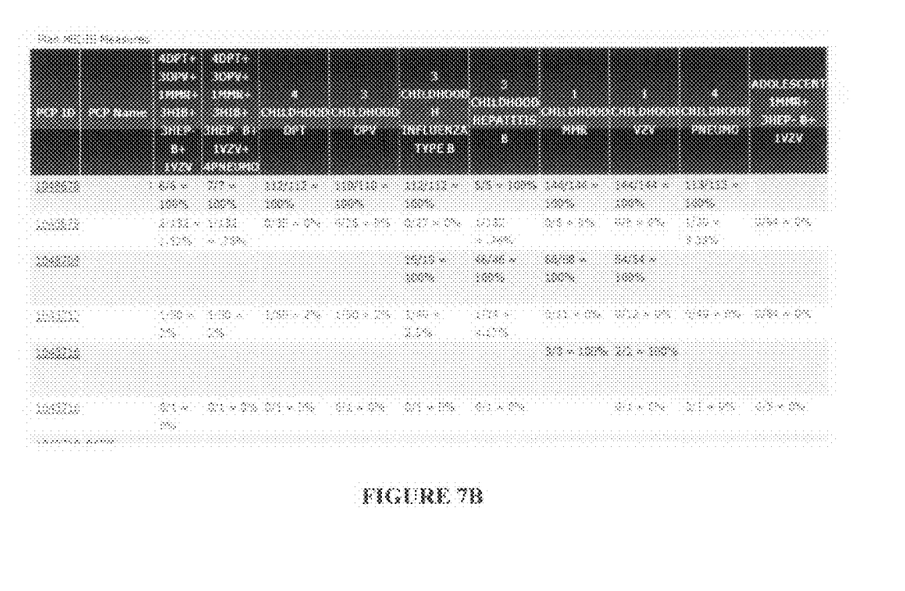
FIG. 7B exemplarily illustrates a screen display of the individual quality index of each of the primary care physicians for each of the predetermined measures.

The quality index calculator 201f calculates quality indexes for the PCPs 203 for the implemented predetermined measures. The step of calculating the quality indexes for the PCPs 203 comprises calculating an individual quality index for each of the predetermined measures, a relative quality index for each of the predetermined measures, and a total quality index for each of the PCPs 203. FIG. 7A exemplarily illustrates the calculation of the quality indexes for the primary care physicians 203 for the implemented predetermined measures. The individual quality index is the ratio of the number of members 202 of the PCPs 203 that are already measured for the predetermined measures to the total number of identified members 202 of the PCPs 203. FIG. 7B exemplarily illustrates a screen display of the individual quality index of each of the primary care physicians 203 for each of the predetermined measures.

The quality index calculator 201f also calculates the relative quality index for each of the PCPs 203 as the ratio of the performance score of the health plan for each of the predetermined measures to the individual quality index of each of the PCPs 203. The relative quality index for each of the PCPs 203 is given by the following formula:

Relative quality index for a PCP for a predetermined measure=Health Plan's performance score of the predetermined measure/individual quality index of the PCP for that predetermined measure.

The quality index calculator 201f also calculates the total quality index for each of the PCPs 203. The total quality index is calculated as the average of the relative quality indexes of all the predetermined measures for each of the PCPs 203. The formula for the total quality index for each of the PCPs 203 is computed as follows:

Total quality index of a PCP=Sum of the relative quality indexes of all the predetermined measures of the PCP/Number of predetermined measures.

The total quality index for each of the PCPs 203 is compared with a predetermined threshold value to determine performance of the PCPs 203. The total quality index is used for designing pay for performance programs for each of the PCPs 203. The total quality index of each of the PCPs 203 indicates the performance of the PCPs 203 in the health plan. The performance of the PCP is determined by checking whether the total quality index is greater or less than a predefined value. For example, a total quality index less than 1 indicates good performance by a PCP, whereas a total quality index greater than 1 indicates that the PCP is required to improve performance. Consider the example illustrated in FIG. 7A. The following calculations are made for PCP1 and PCP2 on Measure1 and Measure2:

Health Plan's Performance Score for Measure1=0.60

Health Plan's Performance Score for Measure2=0.50

Quality Index of PCP1 for Measure1=0.66

Quality Index of PCP1 for Measure2=0.66

Relative Quality Index of PCP1 for Measure1=0.6/0.66=0.90

Relative Quality Index of PCP1 for Measure2=0.5/0.66=0.75

Total Quality Index of PCP1=(0.9+0.75)/2=0.83

Quality Index of PCP2 for Measure1=0.50

Quality Index of PCP2 for Measure2=0.40

Relative Quality Index of PCP2 for Measure1=0.6/0.5=1.2

Relative Quality Index of PCP2 for Measure2=0.5/0.4=1.25

Total Quality Index of PCP2=(1.2+1.25)/2=1.225

The above calculations shows that since the total quality index of PCP1 is less than 1, PCP1 has met the requirements of the health plan, thereby resulting in better performance of PCP1. The total quality index of PCP2 is greater than 1 which indicates that PCP2 needs to improve performance. Effective incentive programs and pay for performance programs may be designed to reward effective PCPs 203. The health plan administrators may review the performance of the PCPs 203. The PCPs 203 who have not met the required percentage specified by the health plan are notified and reminded to follow-up on their members 202. The PCPs 203 performance may also be compared with national benchmarks for different HEDIS measures. The total quality index of each of the PCPs 203 calculated by the score calculator 201e are stored in the health care database 201h. The analysis of performance ensures increased quality by PCPs 203, reduced level of chart review by the health plan staff 204, improved health of the members 202 and subsequent reduction in overall medical costs.

It will be readily apparent that the various methods and algorithms described herein may be implemented in a computer readable medium appropriately programmed for general purpose computers and computing devices. Typically a processor, for e.g., one or more microprocessors will receive instructions from a memory or like device, and execute those instructions, thereby performing one or more processes defined by those instructions. Further, programs that implement such methods and algorithms may be stored and transmitted using a variety of media, for e.g., computer readable media in a number of manners. In one embodiment, hard-wired circuitry or custom hardware may be used in place of, or in combination with, software instructions for implementation of the processes of various embodiments. Thus, embodiments are not limited to any specific combination of hardware and software. A 'processor' means any one or more microprocessors, Central Processing Unit (CPU) devices, computing devices, microcontrollers, digital signal processors or like devices. The term 'computer-readable medium' refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include Dynamic Random Access Memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during Radio Frequency (RF) and Infrared (IR) data communications. Common forms of computer-readable media include, for example, a floppy disk, a flexible disk, hard disk, magnetic tape, any other magnetic medium, a Compact Disc-Read Only Memory (CD-ROM), Digital Versatile Disc (DVD), any other optical medium, punch cards, paper tape, any other physical medium with patterns of holes, a Random Access Memory (RAM), a Programmable Read Only Memory (PROM), an Erasable Programmable Read Only Memory (EPROM), an Electrically Erasable Programmable Read Only Memory (EEPROM), a flash memory, any other memory chip or cartridge, a carrier wave as described hereinafter, or any other medium from which a computer can read. In general, the computer-readable programs may be implemented in any programming language. Some examples of languages that can be used include C, C++, C#, or JAVA. The software programs may be stored on or in one or more mediums as an object code. A computer program product comprising computer executable instructions embodied in a computer-readable medium comprises computer parsable codes for the implementation of the processes of various embodiments.

Where databases are described such as the health care database 201h, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats including relational databases, object-based models and/or distributed databases could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, Local Area Network (LAN), Wide Area Network (WAN) or Ethernet, Token Ring, or via any appropriate communications means or combination of communications means. Each of the devices may comprise computers, such as those based on the Intel® processors that are adapted to communicate with the computer. Any number and type of machines may be in communication with the computer.

The foregoing examples have been provided merely for the purpose of explanation and are in no way to be construed as limiting of the present method and system disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method of improving the prospective quality of health care in a health plan, comprising the steps of:

provding a prospective health care quality improvement system on a computing device comprising one or more processors;

prospectively identifying members of said health plan that need predetermined measures of said health care by an identification engine on said health care quality improvement system, comprising:

reviewing medical history data of said members, wherein said medical history data provides a list of said predetermined measures pending for a member and a list of predetermined measures implemented for said member, wherein said predetermined measures and information of said identified members are stored in a health care database, and wherein the predetermined measures of healthcare cover both disease related and preventive measures;

prospectively identifying primary care physicians for said identified members by said identification engine, wherein information of said identified primary care physicians is stored in said health care database;

prospectively notifying the identified members to undergo said predetermined measures by a notification engine on said health care quality improvement system, using said information of said identified members accessed from said health care database;

prospectively notifying said primary care physicians to ensure implementation of the predetermined measures pending for the identified members by said notification engine, using said information of said primary care physicians accessed from said health care database;

prospectively notifying staff of the health plan to ensure coordination between the identified members and the primary care physicians, and direct coordination with the identified members without the primary care physicians by said notification engine;

prospectively implementing said pending predetermined measures by said primary care physicians for said disease related and said preventive measures on said identified members;

prospectively updating status of said implemented predetermined measures of the identified members on an online user interface provided by an updation engine and storing said updated status in said health care database; and prospectively calculating a performance score of the health plan for each of the predetermined measures to indicate said quality of health care in the health plan to allow the health care staff to prospectively take appropriate steps to improve said quality of health care, wherein the performance score is the ratio of said identified members on whom said predetermined measures have been implemented as indicated on said online user interface to total number of identified members for the predetermined measure of said health plan;

whereby said step of prospectively calculating the performance score and communicating the pending predetermined measures that are due to the primary care physician, the health plan staff and the member facilitates the completion of the measures and proactively of the health plan improves the quality of health care in the health plan.

2. The computer implemented method of claim 1, wherein the members of the health plan are one of individual consumers and employees of companies requiring health care, wherein said companies provide health benefits to said employees, and to Medicare and Medicaid members.

3. The computer implemented method of claim 1, wherein the members of the health plan are identified based on age, gender and pre-existing disease conditions.

4. The computer implemented method of claim 1, wherein the predetermined measures belong to domains including effectiveness of health care, availability of heath care, satisfaction with the experience of health care, health plan stability, use of services, cost of health care, informed health care choices, and health care descriptive information.

5. The computer implemented method of claim 1, wherein said step of notifying the identified members, the primary care physicians, and the health plan staff is performed by an electronic means including electronic mail, fax, and automated voice messages.

6. The computer implemented method of claim 1, further comprises calculating quality indexes for the primary care physicians for the implemented predetermined measures, wherein said step of calculating the quality indexes for the primary care physicians comprises calculating an individual quality index, a relative quality index, and a total quality index for each of the primary care physicians, and wherein said individual quality index, said relative quality index, and said total quality index are calculated for each of the predetermined measures.

7. The computer implemented method of claim 6, wherein the individual quality index of each of the primary care physicians is the ratio of the number of measured members of the primary care physicians to the total number of identified members of the primary care physicians, wherein said measured members have undergone the predetermined measures.

8. The computer implemented method of claim 6, wherein the relative quality index of each of the primary care physicians is the ratio of the performance score of the health plan for each of the predetermined measures to the individual quality index of the primary care physician for the predetermined-measure.

9. The computer implemented method of claim 6, wherein said total quality index of each of the primary care physicians is the average of the relative quality indexes of the implemented predetermined measures for the primary care physicians.

10. The computer implemented method of claim 9, wherein the total quality index of each of the primary care physicians is compared with a predetermined threshold value to determine performance of the primary care physicians.

11. The computer implemented method of claim 9, wherein the total quality index of each of the primary care physicians is used for designing pay for performance programs for each of the primary care physicians.

12. The computer implemented method of claim 1, wherein the performance score for each of the predetermined measures of the health plan is used for comparing performance of the health plan with predetermined performance benchmarks.

13. The computer implemented method of claim 12, wherein said predetermined performance benchmarks are one of national benchmarks and regional benchmarks.

14. A computer implemented system for improving the prospective quality of health care in a health plan, comprising:
   a computer system comprising one or more processors, said computer system hosting an intelligent health care quality improvement system, comprising:
      an identification engine configured to prospectively identify members of said health plan eligible for undergoing predetermined measures of said health care and primary care physicians for said identified members, wherein said members are identified based on review of medical history data of said members, wherein said medical history data provides a list of said predetermined measures pending for a member and a list of predetermined measures implemented for said member, and wherein said identification engine displays said medical history data of said members on a display screen associated with said computer system;
      a notification engine configured to prospectively notify the identified members, said primary care physicians to ensure implementation of said predetermined measures pending for said identified members, and staff of the health plan to ensure coordination between the identified members and the primary care physicians, and direct coordination with the identified members without the primary care physicians;
      an updation engine comprising an online user interface configured to prospectively update status of the identified members based on said implemented predetermined measures by the primary care physicians;
      a performance analyzer configured to analyze performance of the health plan, comprising:
         a score calculator configured to calculate, using said processors, a performance score of the health plan for each of the predetermined measures; and
         a quality index calculator configured to calculate, using said processors, quality indexes for the primary care physicians for the implemented predetermined measures;
      a health care database configured to store information on the predetermined measures, information on the members, information of the primary care physicians, and the performance score of the health plan.

15. The computer implemented system of claim 14, wherein said intelligent health care quality improvement system further comprises a scheduler configured to prospectively schedule said steps of identifying and notifying said members, the primary care physicians, and said health plan staff.

16. The computer implemented system of claim 15, wherein said scheduler prospectively schedules a step of updating the implemented predetermined measures by the primary care physicians.

17. The computer implemented system of claim 14, wherein said member information comprises names of the members, said medical history data of the members, and status of the members based on the predetermined measures.

18. The computer implemented system of claim 14, wherein said primary care physician information comprises names of the primary care physicians, the names of the members of the primary care physicians, and said quality indexes of the primary care physicians.

19. A computer program product comprising computer executable instructions embodied in a non-transitory computer-readable medium, wherein said computer program product comprises:
   a first computer parsable program code means for prospectively identifying members of a health plan eligible for undergoing predetermined measures of health care, wherein said first computer parsable program code means reviews medical history data of said members, wherein said medical history data provides a list of said predetermined measures pending for a member and a list of predetermined measures implemented for said member, and wherein the predetermined measures of healthcare cover both disease related and preventive measures;
   a second computer parsable program code means for prospectively identifying primary care physicians for said identified members;
   a third computer parsable program code means for prospectively notifying the identified members to undergo said predetermined measures;
   a fourth computer parsable program code means for prospectively notifying said primary care physicians to ensure implementation of the predetermined measures for the identified members;
   a fifth computer parsable program code means for prospectively notifying staff of said health plan to ensure coordination between the identified members and the primary care physicians, and direct coordination with the identified members without the primary care physicians;
   a sixth computer parsable program code means that provides an online user interface for prospectively updating status of the identified members based on said implemented predetermined measures by the primary care physicians;
   a seventh computer parsable program code means for calculating quality indexes for the primary care physicians for the implemented predetermined measures; and
   an eighth computer parsable program code means for calculating a performance score of the health plan for each of the predetermined measures to indicate said quality of said health care in the health plan.

20. The computer program product of claim 19, further comprising a ninth computer parsable program code means configured to calculate an individual quality index, a relative quality index, and a total quality index for each of the primary care physicians, wherein said individual quality index and said relative quality index are calculated for each of the predetermined measures.

21. The computer program product of claim 20, further comprising a tenth computer parsable program code means configured to compare said total quality index of each of the primary care physicians with a predetermined threshold value to determine performance of the primary care physicians.

22. The computer program product of claim 21, further comprising an eleventh computer parsable program code means configured to design pay for performance programs for each of the primary care physicians based on the total quality index.

23. A computer implemented method of improving the prospective quality of health care in a health plan, comprising the steps of:
   providing a prospective health care quality improvement system on a computing device comprising one or more processors;

prospectively identifying members of said health plan eligible for undergoing predetermined measures of said health care by an identification engine on said health care quality improvement system, comprising:
reviewing medical history data of said members, wherein said medical history data provides a list of said predetermined measures pending for a member and a list of predetermined measures implemented for said member, wherein said predetermined measures and information of said identified members are stored in a health care database, and wherein said predetermined measures comprise disease related and preventive measures;
prospectively identifying primary care physicians for said identified members by said identification engine, wherein information of said identified primary care physicians is stored in said health care database;
prospectively notifying the identified members and said primary care physicians by said notification engine to ensure implementation of the e predetermined measures for the identified members, using said information of said primary care physicians and said identified members stored in said health care database;
prospectively implementing said predetermined measures by said primary care physicians;
prospectively updating status of the identified members on an online user interface provided by an updation engine based on said implemented predetermined measures by the primary care physicians;
prospectively calculating a performance score for the health plan for each of the predetermined measures, wherein said performance score of a predetermined measure is a ratio of number of said members of the health plan with said implemented predetermined measure to total number of said identified members with said pending predetermined measures; and
prospectively calculating a plurality of quality indexes for the primary care physicians for the implemented predetermined measures by a quality index calculator, comprising:
calculating an individual quality index of each of the primary care physicians, wherein said individual quality index is the ratio of the number members of the primary care physicians with implemented predetermined measures the to the total number of identified members of the primary care physicians;
calculating a relative quality index of each of the primary care physicians, wherein said relative quality index is the ratio of the performance score of the health plan for each of the predetermined measures to the individual quality index of the primary care physician for the predetermined-measure; and
calculating a total quality index for each of said primary care physicians, wherein said total quality index is an average of said relative quality indexes of said predetermined measures for each of said primary care physicians;
whereby said steps of identifying and notifying said members and said primary care physicians about the predetermined measures reduces level of patient chart review to prevent said disease and manage disease conditions.

24. A computer implemented method of prospectively improving the quality of health care in a health plan by reducing level of patient chart review by health plan staff, comprising the steps of:
providing a prospective health care quality improvement system on a computing device comprising one or more processors;
prospectively identifying members of said health plan eligible for undergoing predetermined measures of said health care by an identification engine on said health care quality improvement system, comprising:
reviewing medical history data of said members, wherein said medical history data provides a list of said predetermined measures pending for a member and a list of predetermined measures implemented for said member, wherein said predetermined measures and information of said identified members are stored in a health care database;
prospectively identifying primary care physicians for said identified members by said identification engine, wherein information of said identified primary care physicians is stored in said health care database;
prospectively notifying the identified members to undergo said predetermined measures by a notification engine on said health care quality improvement system, using said information of said identified members accessed from said health care database;
prospectively notifying said staff of the health plan to ensure coordination between the identified members and the primary care physicians, and direct coordination with the identified members without the primary care physicians by said notification engine;
implementing said pending predetermined measures by said primary care physicians on said identified members;
prospectively updating status of the identified members on an online user interface provided by an updation engine based on said implemented predetermined measures by the primary care physicians, wherein said updation engine is provided by said health care quality improvement system and said updated status is stored in said health care database; and
prospectively analyzing performance of said primary care physicians for increasing quality of implementation of said predetermined measures and for reducing said level of patient chart review by the health plan staff.

25. A computer implemented method of prospectively providing information of performance of a primary care physician for improving the quality of health care in a health plan, comprising the steps of:
prospectively providing a health care quality improvement system on a computing device comprising one or more processors;
prospectively identifying members of said health plan that need predetermined measures of said health care by an identification engine on said health care quality improvement system, comprising:
reviewing medical history data of said members, wherein said medical history data provides a list of said predetermined measures pending for a member and a list of predetermined measures implemented for said member, wherein said predetermined measures and information of said identified members are stored in a health care database, and wherein the predetermined measures of healthcare cover both disease related and preventive measures;
prospectively identifying primary care physicians for said identified members by said identification engine, wherein information of said identified primary care physicians is stored in said health care database;

prospectively notifying the identified members to undergo said predetermined measures by a notification engine on said health care quality improvement system, using said information of said identified members accessed from said health care database;

prospectively notifying said primary care physicians to ensure implementation of the e predetermined measures pending for the identified members by said notification engine, using said information of said primary care physicians accessed from said health care database;

prospectively notifying staff of the health plan to ensure coordination between the identified members and the primary care physicians, and direct coordination with the identified members without the primary care physicians by said notification engine;

prospectively implementing said pending predetermined measures by said primary care physicians on said identified members;

prospectively updating status of said implemented predetermined measures of the identified members on an online user interface provided by an updation engine, wherein said updation engine is provided by said health care quality improvement system and said updated status is stored in said health care database;

calculating a performance score of the health plan for each of the predetermined measures to indicate said quality of health care in the health plan, wherein the performance score for a predetermined measure of the health plan is the ratio of the number of the members of the health plan already measured for said predetermined measure to the total number of the identified members for the predetermined measure in the health plan;

comparing said performance score of the health plan for each of the predetermined measures with corresponding predetermined performance benchmarks; and calculating a total quality index for each of the primary care physicians using the performance score of the health plan for each of the predetermined measures;

whereby said steps of calculating the performance score and the total quality index provides information on the performance of said primary care physician and thereby improves the quality of health care in the health plan.

26. A computer implemented method of improving the prospective quality of health care in a health plan, comprising the steps of:

providing a prospective health care quality improvement system on a computing device comprising one or more processors;

prospectively identifying members of said health plan that need predetermined measures of said health care by an identification engine on said health care quality improvement system, comprising:
reviewing medical history data of said members, wherein said medical history data provides a list of said predetermined measures pending for a member and a list of predetermined measures implemented for said member, wherein said predetermined measures and information of said identified members are stored in a health care database, and wherein the predetermined measures of healthcare cover both disease related and preventive measures;

prospectively identifying primary care physicians for said identified members by said identification engine, wherein information of said identified primary care physicians is stored in said health care database;

prospectively notifying the identified members to undergo said predetermined measures by a notification engine on said health care quality improvement system, using said information of said identified members accessed from said health care database;

prospectively notifying said primary care physicians to ensure implementation of the predetermined measures pending for the identified members by said notification engine, using said information of said primary care physicians accessed from said health care database;

prospectively notifying staff of the health plan to ensure coordination between the identified members and the primary care physicians, and direct coordination with the identified members without the primary care physicians by said notification engine;

prospectively implementing said pending predetermined measures by said primary care physicians on said identified members;

prospectively updating status of said implemented predetermined measures of the identified members on an online user interface provided by an updation engine and storing said updated status in a health care database; and reducing patient chart review of the identified members by conducting said patient chart review online on said stored updated status of the implemented predetermined measures of the identified members by the health plan staff;

whereby said step of reducing patient chart review of the identified members reduces the cost of health care in the health plan.

* * * * *